(12) United States Patent  
Grother et al.

(10) Patent No.: US 11,517,533 B2  
(45) Date of Patent: Dec. 6, 2022

(54) COMPOSITIONS OF DIFFERENT DENSITIES FOR FAST DISINTEGRATING MULTI-LAYER TABLET

(71) Applicant: Catalent U.K. Swindon Zydis Limited, Swindon (GB)

(72) Inventors: Leon Paul Grother, Swindon (GB); Keiko Tsutsumi, Swindon (GB); Rosaleen Theresa McLaughlin, Swindon (GB); Yik Teng Wong, Swindon (GB)

(73) Assignee: Catalent U.K. Swindon Zydis Limited, Swindon (GB)

(*) Notice: Subject to any disclaimer, the term of this patent is extended or adjusted under 35 U.S.C. 154(b) by 167 days.

(21) Appl. No.: 16/344,861

(22) PCT Filed: Oct. 25, 2017

(86) PCT No.: PCT/IB2017/056633  
§ 371 (c)(1),  
(2) Date: Apr. 25, 2019

(87) PCT Pub. No.: WO2018/078548  
PCT Pub. Date: May 3, 2018

(65) Prior Publication Data  
US 2020/0138721 A1 May 7, 2020

Related U.S. Application Data

(60) Provisional application No. 62/412,528, filed on Oct. 25, 2016.

(51) Int. Cl.  
*A61K 9/19* (2006.01)  
*A61K 9/20* (2006.01)  
(Continued)

(52) U.S. Cl.  
CPC .............. *A61K 9/2095* (2013.01); *A61K 9/19* (2013.01); *A61K 9/2086* (2013.01);  
(Continued)

(58) Field of Classification Search  
CPC ................................ A61K 9/19; A61K 9/2086  
See application file for complete search history.

(56) References Cited

U.S. PATENT DOCUMENTS 5,044,091 A 9/1991 Ueda et al.  
6,709,669 B1 3/2004 Murray et al.  
(Continued)

FOREIGN PATENT DOCUMENTS

EP 1110541 6/2001  
EP 1980245 10/2008  
(Continued)

OTHER PUBLICATIONS

Manufacturing Chemist. (Sep. 13, 2016) "Patient-centric dose design," located at https://www.manufacturingchemist.com/news/article_page/Patient-centric_dose_design/120927 visited on Sep. 25, 2020. (4 pages).

(Continued)

*Primary Examiner* — Bethany P Barham  
*Assistant Examiner* — Barbara S Frazier  
(74) *Attorney, Agent, or Firm* — Morrison & Foerster LLP

(57) ABSTRACT

Described herein is a method for forming multi-layer drug dosage forms having at least two layers. In the method, a first formulation comprising a non-gelling matrix forming agent and having a first density is dosed into a preformed mold. A second formulation comprising a non-gelling matrix former and having a second density not equal to the first density is subsequently dosed into the preformed mold. Then, the combination of the formulations dosed into the (Continued)

Table 2

| Layer Number [Formulation Nos] | Product 1 | | Product 2 | | Product 3 | | Product 4 | |
|---|---|---|---|---|---|---|---|---|
| | 1st dosing layer | 2nd dosing layer | 1st dosing layer | 2nd dosing layer | 1st dosing layer | 2nd dosing layer | 1st dosing layer | 2nd dosing layer |
| Assessment of bilayer | Absence of 2 distinct phases | | Absence of 2 distinct phases | | Presence of 2 phases. The bottom layer contains buffer salt | | Presence of 2 phases. The bottom layer contains buffer salt | | mold is freeze dried to form the multi-layer dosage form having at least two layers. The use of a density difference between the first and second formulations ensures formation of a product with two distinct layers.

9 Claims, 14 Drawing Sheets

(51) Int. Cl.
    *A61K 47/26*     (2006.01)
    *A61K 47/42*     (2017.01)
    *A61K 31/137*     (2006.01)
    *A61K 31/138*     (2006.01)

(52) U.S. Cl.
    CPC .......... *A61K 31/137* (2013.01); *A61K 31/138* (2013.01); *A61K 47/26* (2013.01); *A61K 47/42* (2013.01)

(56) References Cited

U.S. PATENT DOCUMENTS

| | | | |
|---|---|---|---|
| 2011/0213036 A1* | 9/2011 | Park | A61K 6/20 |
| | | | 514/574 |
| 2011/0229573 A1* | 9/2011 | Tian | A61P 7/02 |
| | | | 424/488 |

FOREIGN PATENT DOCUMENTS

| | | |
|---|---|---|
| FR | 1373287 A | 9/1964 |
| GB | 1548022 | 7/1979 |
| JP | 2003-524622 A | 8/2003 |
| JP | 2013-522308 A | 6/2013 |
| WO | 00/61117 A1 | 10/2000 |
| WO | 2004/066924 | 8/2004 |
| WO | 2006/063189 | 6/2006 |
| WO | 2011/115969 A2 | 9/2011 |

OTHER PUBLICATIONS

Notice of Reasons for Rejection dated Oct. 5, 2020, directed to JP Application No. 2019-542823; 12 pages.

International Search Report and Written Opinion dated Feb. 8, 2018, directed to International Application No. PCT/IB2017/056633; 12 pages.

Office Action dated Mar. 16, 2021, directed to EP Application No. 17801499.9; 4 pages.

\* cited by examiner

Table 2

| Layer Number [Formulation Nos] | Product 1 | | Product 2 | | Product 3 | | Product 4 | |
|---|---|---|---|---|---|---|---|---|
| | 1st dosing layer | 2nd dosing layer | 1st dosing layer | 2nd dosing layer | 1st dosing layer | 2nd dosing layer | 1st dosing layer | 2nd dosing layer |
| Assessment of bilayer | Absence of 2 distinct phases | | Absence of 2 distinct phases | | Presence of 2 phases. The bottom layer contains buffer salt | | Presence of 2 phases. The bottom layer contains buffer salt | |

FIG. 1

Table 3

| Layer Number [Formulation Nos] | Product 5 | | Product 6 | | Product 7 | | Product 8 | |
|---|---|---|---|---|---|---|---|---|
| | 1st dosing layer | 2nd dosing layer | 1st dosing layer | 2nd dosing layer | 1st dosing layer | 2nd dosing layer | 1st dosing layer | 2nd dosing layer |
| Dosing temp (°C) | 23 | 23 | 23 | 23 | 23 | 23 | 23 | 23 |
| Aliquot Dosing weight (mg) | 300 | 300 | 300 | 300 | 300 | 300 | 300 | 300 |
| Composition | | | | | | | | |
| Fish gelatin | 5% | 5% | 5% | 5% | 5% | 5% | 5% | 5% |
| Mannitol | 3% | 3% | 3% | 3% | 3% | 3% | 3% | 3% |
| Sodium phosphate dibasic | 2% | 0% | 0% | 2% | 1% | 0% | 0% | 1% |
| Brilliant Blue | N/A | 0.01% | 0.01% | N/A | N/A | 0.01% | 0.01% | N/A |
| Testing | | | | | | | | |
| pH | 8.42 | 6.47 | 6.47 | 8.42 | 8.17 | 6.47 | 6.47 | 8.17 |
| Overall pH upon reconstitution of tablet | 8.16 | | N/R | | 7.90 | | N/R | |
| Viscosity (mPa.s) | 8.8 | 7.4 | 7.4 | 8.8 | 8.4 | 7.4 | 7.4 | 8.4 |
| Viscosity difference bet layers | 1.4 mPa.s | | 1.4 mPa.s | | 1.0 mPa.s | | 1.0 mPa.s | |
| Solution Density (g/ml) | 1.043 | 1.022 | 1.022 | 1.043 | 1.032 | 1.022 | 1.022 | 1.032 |

Table 3

| | Product 5 | Product 6 | Product 7 | Product 8 |
|---|---|---|---|---|
| Density difference between layer | 0.021 | 0.021 | 0.010 | 0.010 |
| Presence of 2 layers. Layer with buffer salt (no dye) is at the bottom irrespective of the order of dosing sequence. | | | | |

FIG. 2B

Table 4

| Layer Number [Formulation Nos] | Product 9 | | Product 10 | | Product 11 | |
|---|---|---|---|---|---|---|
| | 1st dosing layer | 2nd dosing layer | 1st dosing layer | 2nd dosing layer | 1st dosing layer | 2nd dosing layer |
| Dosing temp (°C) | 23 | 23 | 23 | 23 | 23 | 23 |
| Aliquot Dosing weight (mg) | 300 | 300 | 300 | 300 | 300 | 300 |
| Composition | | | | | | |
| Fish gelatin | 6% | 6% | 6% | 6% | 6% | 6% |
| Mannitol | 3% | 3% | 3% | 3% | 3% | 3% |
| Sodium phosphate dibasic | 3% | 0% | 5% | 0% | 7% | 0% |
| Brilliant Blue | N/A | 0.01% | N/A | 0.01% | N/A | 0.01% |
| Testing | | | | | | |
| Viscosity (mPa.s) | 5.3 | 5.2 | 5.8 | 5.2 | 6.1 | 5.2 |
| Viscosity difference bet layers | 0.1 mPa.s | | 0.6 mPa.s | | 0.9 mPa.s | |
| pH | 7.92 | 5.13 | 8.02 | 5.13 | 8.12 | 5.13 |
| Solution Density [g/ml] | 1.055 | 1.026 | 1.075 | 1.026 | 1.095 | 1.026 |
| Density difference between layer | 0.029 | | 0.049 | | 0.069 | |
| Overall pH upon reconstitution of tablet | 7.66 | | 7.80 | | 7.95 | |
| Distinct bilayer tablet with the layer denser containing buffer salt at the bottom | 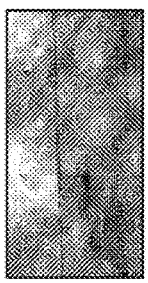 | | 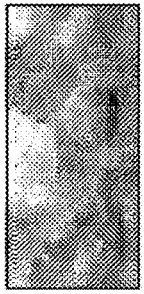 | | 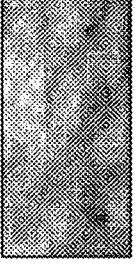 | |

FIG. 3

Table 5
| Layer Number [Formulation Nos] | Product 12 | | Product 13 | | Product 14 | |
|---|---|---|---|---|---|---|
| | 1st dosing layer | 2nd dosing layer | 1st dosing layer | 2nd dosing layer | 1st dosing layer | 2nd dosing layer |
| Distinct bilayer tablet with the layer denser containing buffer salt at the bottom | 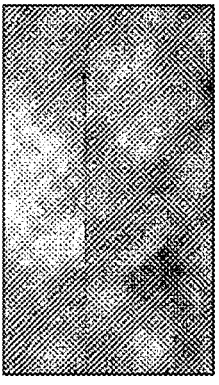 | | 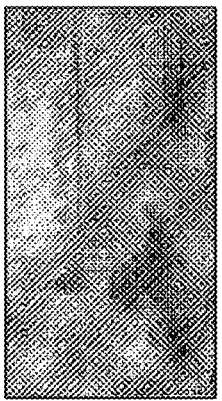 | | 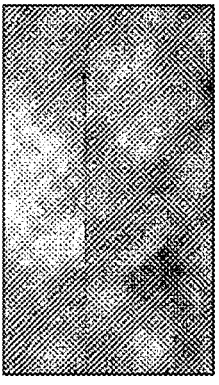 | |
FIG. 4

Table 6

| | Product 15 | | Product 16 | | Product 17 | |
|---|---|---|---|---|---|---|
| Layer Number [Formulation Nos] | 1st dosing layer | 2nd dosing layer | 1st dosing layer | 2nd dosing layer | 1st dosing layer | 2nd dosing layer |
| Dosing temp (°C) | 23 | 23 | 23 | 23 | 23 | 23 |
| Aliquot Dosing weight (mg) | 300 | 300 | 300 | 300 | 300 | 300 |
| Composition | | | | | | |
| Diphenydramine HCl | N/A | 3.3% | N/A | 0.4% | N/A | 0.4% |
| Fish gelatin | 5% | 5% | 5% | 5% | 6% | 6% |
| Mannitol | 3% | 3% | 3% | 3% | 3% | 3% |
| Sodium phosphate dibasic | 3% | 0% | 3% | 0% | 3% | 0% |
| Brilliant Blue | N/A | 0.01% | N/A | 0.01% | N/A | 0.01% |
| Testing | | | | | | |
| Viscosity (mPa.s) | 10.3 | 9.8 | 10.3 | 8.9 | 6.3 | 4.9 |
| Viscosity difference bet layers | 2.01 mPa.s | | 1.4 mPa.s | | 1.4 mPa.s | |
| pH | 8.47 | 6.31 | 8.12 | 6.51 | 7.88 | 5.19 |
| Overall pH upon reconstitution of tablet | 7.75 | | 8.11 | | 7.70 | |
| Solution Density [g/ml] | 1.053 | 1.029 | 1.053 | 1.025 | 1.055 | 1.029 |
| Density difference between layer | 0.024 | | 0.028 | | 0.026 | |

Table 7

| | Product 18 | | Product 19 | |
|---|---|---|---|---|
| Layer Number [Formulation Nos] | 1st dosing layer | 2nd dosing layer | 1st dosing layer | 2nd dosing layer |
| Dosing temp (°C) | 23 | 23 | 23 | 23 |
| Aliquot Dosing weight (mg) | 250 | 250 | 300 | 300 |
| Composition | | | | |
| Selegiline HCl | N/A | 0.5% | N/A | 0.5% |
| Fish gelatin | 5% | 5% | 5% | 5% |
| Mannitol | 3% | 3% | 3% | 3% |
| Sodium phosphate dibasic | 3% | 0% | 1% | 0% |
| Brilliant Blue | N/A | 0.01% | N/A | 0.01% |
| Testing | | | | |
| Viscosity (mPa.s) | 9.5 | 9.4 | 9.5 | 9.4 |
| Viscosity difference bet layers | 0.1 mPa.s | | 0.1 mPa.s | |
| pH | 8.45 | 6.11 | 8.09 | 6.11 |
| Overall pH upon reconstitution of tablet | 7.59 | | 7.33 | |
| Solution Density [g/ml] | 1.053 | 1.025 | 1.032 | 1.025 |
| Density difference between layer | 0.028 | | 0.007 | |

Table 8

| Layer Number [Formulation Nos] | Product 20 | | Product 21 | |
|---|---|---|---|---|
| | 1st dosing layer | 2nd dosing layer | 1st dosing layer | 2nd dosing layer |
| Dosing temp (°C) | 23 | 23 | 23 | 23 |
| Aliquot Dosing weight (mg) | 250 | 250 | 300 | 300 |
| Composition | | | | |
| Selegiline HCl | - | 0.5% | - | 0.5% |
| Fish gelatin | 6% | 6% | 6% | 6% |
| Mannitol | 3% | 3% | 3% | 3% |
| Sodium phosphate dibasic | 3% | 0% | 1% | 0% |
| Brilliant Blue | - | 0.01% | - | 0.01% |
| Testing | | | | |
| Viscosity (mPa.s) | 9.5 | 9.4 | 8.4 | 9.4 |
| Viscosity difference bet layers | 0.1 mPa.s | | 1.0 mPa.s | |
| pH | 7.88 | 5.16 | 7.44 | 5.16 |
| Overall pH upon reconstitution of tablet | 7.38 | | 7.10 | |
| Solution Density (g/ml) | 1.055 | 1.029 | 1.036 | 1.029 |
| Density difference between layer | 0.026 | | 0.007 | |

FIG. 7A  TO FIG. 7B

Table 9

| Layer Number [Formulation Nos] | Product 22 | | Product 23 | | Product 24 | |
|---|---|---|---|---|---|---|
| | 1st dosing layer | 2nd dosing layer | 1st dosing layer | 2nd dosing layer | 1st dosing layer | 2nd dosing layer |
| Dosing temp (°C) | 23 | 23 | 23 | 23 | 23 | 23 |
| Aliquot Dosing weight (mg) | 250 | 250 | 250 | 250 | 250 | 250 |
| Composition | | | | | | |
| Thiamine HCl | - | - | - | - | 0.4 | 0% |
| Fish gelatin | 5% | 5% | 5% | 5% | 5% | 5% |
| Mannitol | 3% | 3% | 3% | 3% | 3% | 3% |
| Citric acid | 5% | 0% | 1% | 0% | 3% | 0% |
| Brilliant Blue | - | 0.01% | - | 0.01% | - | 0.01% |
| Testing | | | | | | |
| Viscosity (mPa.s) | 14.9 | 8.7 | 12.2 | 8.7 | 13.2 | 8.7 |
| Viscosity difference bet layers | 6.01 mPa.s | | 3.5 mPa.s | | 4.5 mPa.s | |
| pH | 2.06 | 5.39 | 2.88 | 5.39 | 2.16 | 5.39 |
| Overall pH upon reconstitution of tablet | 2.65 | | 3.72 | | 2.89 | |
| Solution Density (g/ml) | 1.044 | 1.022 | 1.027 | 1.022 | 1.038 | 1.022 |
| Density difference between layer | 0.022 | | 0.005 | | 0.016 | |

FIG. 8A   TO FIG. 8B

COMPOSITIONS OF DIFFERENT DENSITIES FOR FAST DISINTEGRATING MULTI-LAYER TABLET

REFERENCE TO RELATED APPLICATIONS

This application is a national stage application under 35 USC 371 of International Application No. PCT/IB2017/056633, filed Oct. 25, 2016, which claims priority to U.S. Provisional Application No. 62/412,528, filed Oct. 25, 2016, the entire contents of each of which are incorporated herein by reference.

FIELD OF THE INVENTION

The present invention relates to the use of density modifiers in active compositions including solution formulations containing matrix formers suitable for lyophilization to form a multi-layer tablet by creating two, or more, formulations exhibiting different densities.

BACKGROUND OF THE INVENTION

Pharmaceutical or active ingredients are provided to patients using a wide variety of dosage forms. A common dosage form for oral ingestion is an orally disintegrating tablet (ODT). ODTs have been formed using a wide variety of techniques, including compression and lyophilization. The freeze-drying process such as is used to make the Zydis® dosage form is often preferred due to the tablet's faster disintegration time, smoother mouth feel, potential for improved pre-gastric absorption, and increased storage options.

It is also desirable to form an orally disintegrating tablet having two or more layers. There are various situations for which a multi-layer dosage form would be beneficial, including: when the active pharmaceutical ingredient ("API") is incompatible with excipients that are essential for the product (e.g. flavoring, sweeteners, and buffering systems); when the pH required for the stability of the API differs from the pH requirement for mucosal absorption; for products having a combination of APIs wherein each ingredient requires a different condition (e.g. pH) for stability and processing; when the APIs require different release profiles; and in other situations as well.

A current approach to creating a multi-layer tablet typically involves sequential dosing of two or more formulations using one of the following methods to vary the viscosities of each layer. One method employs matrix-forming agents with gelling characteristics for forming one layer and non-gelling characteristics for forming the other layer. Other methods employ different concentrations of the selected excipients; adjusting the dosing temperature, or a combination of two or more of these methods.

U.S. Patent Application Publication No. 2011/0229573 discloses a multi-phasio, lyophilized, fast-dissolving dosage form for the delivery of active pharmaceutical ingredients. The preparation is made by sequentially dosing two different formulations of matrix forming agents. Each formulation has a different viscosity. To create the two different viscosities, one of the formulations contains a non-gelling matrix forming agent and the other formulation contains a gelling matrix forming agent. The formulations having different viscosities are dosed into a mold sequentially at different times and temperatures, and the formulation within the mold is processed using a standard freeze drying method.

French Patent No. FR 1373287 discloses a method of lyophilization of compositions containing two or more incompatible APIs in a layer-by-layer process. The layers are created by successive gelation of different solutions in the same container, freezing of these solutions and subsequently freeze drying the multi-layer composition thereby providing a freeze dried multi layered product.

European Patent No. 1 980 245 discloses a formulation and method of making a lyophilized tablet having an upper layer and a base layer. The upper layer contains the API and the base layer is formulated to adhere to the oral mucosa. The tablet is intended to provide delayed, sustained, or extended release of the API(s) and/or excipient(s) relative to the dissolution or disintegration of the upper layer. The two layers are formed by using an API of hydrophilic or lipophilic nature typically as a solution, or suspension (aqueous or oil) for the preparation of a lyophilized upper layer containing fillers, binders, surfactants, flavors, sweeteners, and any combination thereof. The lower layer also contains a gelling matrix forming agent, bioadhesive polymers, permeability enhancers and optional API(s). The bilayer tablet is made using a formulation suitable for lyophilization as the lower layer which is cooled at a temperature between −20° C. and 10° C., adding a formulation suitable for lyophilization for the upper layer onto the base layer, freezing the bilayer system and following with freeze drying.

WO 2004/066924 discloses a pharmaceutical dosage form comprising at least two layers. Each layer is specifically designed for a specific pharmaceutical. One layer is described as containing a proton pump inhibitor. The other layer is described as comprising an aluminum, magnesium, or calcium antacid salt. The dosage form is chewable or rapidly disintegrating. However, there is no mention of a process of manufacturing the dosage form involving sequential dosing of separate solutions or suspensions.

U.S. Pat. No. 5,044,091 describes a freeze-drying method for producing a dried pharmaceutical preparation having two or more layers. The process includes apportioning a first solution into a container, freezing the first layer, then applying a second layer and freezing the second layer on top of the first layer. This process is repeated for the total number of layers desired. The complete preparation is then freeze dried. The interface between layers does not remain completely separate with this process as some diffusion of the solution may occur across the interface. Additionally, there is a possibility that the layers will not adhere properly to each other and the resulting dosage form will not remain intact.

WO 2006/063189 discloses a multi-layered drug delivery system containing at least one tablet layer having at least one medicament and at least one gum layer. The medicament is absorbed through the oral mucosa. The multi-layered drug system is prepared by compression. The gum layer contains a base capable of reacting with a nicotine salt or capable of facilitating conversion of the nicotine salt to a nicotine base. As noted above, compression is not the optimal method for creating a multi-layer dosage form.

The listed methods for creating a multi-layered tablet are not always successful in producing a tablet with two distinct layers. The lack of distinct layers may be due to diffusion of the formulations at the interface between the two layers. Additionally, when the formulations for each of the two layers both contain matrix formers with non-gelling characteristics, a two layer tablet cannot be formed using the approach as described above due to the non-gelling nature of the matrix formers in each layer, which prevents sufficient viscosity differences from being achieved, and results in the two layers diffusing together following dosing to the mold and prior to freezing. A multi-layer dosage form having non-gelling matrix formers in each layer is desirable, and can be needed when different APIs are used in each layer and none of the APIs are compatible with the use of gelling matrix forming agents.

The present invention provides an alternative option for forming a composition having more than one layer that is compatible with the use of non-gelling matrix formers in more than one layer, may have better compatibility with specific active ingredients, and reduces diffusion between the layers, creating more distinct layers in a multi-layer dosage form.

SUMMARY OF THE INVENTION

In a first embodiment, the disclosure relates to a method of forming a multi-layer dosage form having at least two layers including steps of:
  a) dosing a first formulation comprising a non-gelling matrix forming agent and having a first density into a preformed mold;
  b) dosing a second formulation comprising a non-gelling matrix former and having a second density not equal to the first density into the same preformed mold; and
  c) freezing the first and second formulations after steps a-b), and
  d) freeze drying the product of step c) to form the multi-layer dosage form having at least two layers.

One of the first formulation or the second formulation may include a density modifier. The density modifier may be selected from buffer salts, organic weak acids and bases, and a combination of buffer salts and organic weak acids and bases. The density modifier may be present in an amount of from about 0.5% w/w to about 20% w/w based on the total weight of the formulation prior to removal of water by freeze drying.

In each of the foregoing embodiments, the density modifier may be citric acid. In each of the foregoing embodiments, the density modifier may be sodium phosphate dibasic.

In each of the foregoing embodiments, prior to step (c) a difference between the density of the first formulation and the density of the second formulation may be greater than about 0.005 g/ml.

In each of the foregoing embodiments, steps (a) and (b) may be carried out at a temperature from about 5° C. to about 30° C.

In other embodiments, the disclosure relates to a multi-layer dosage form made by any embodiment of the process described above.

In yet another embodiment, the disclosure relates to a multi-layer, lyophilized, dosage form for the delivery of at least one active ingredient comprising:
  a) a first non-gelled matrix layer including an active ingredient; and
  b) a second non-gelled matrix layer.

In some embodiments of the dosage form, the second non-gelled matrix layer may include a second active ingredient that is different from the active ingredient of said first non-gelled matrix layer. In each of the foregoing embodiments the active ingredient may be coated with one or more coating layers. In each of the foregoing embodiments the active ingredient may be complexed with one or more complexing agents. In such embodiments, the complexing agent may comprise cyclodextrin. The complexed active ingredient may alternatively be complexed with an ion exchange resin.

Soluble density modifiers are used to form a multi-layer tablet by creating two, or more, formulations exhibiting different densities. The two, or more, formulations are dosed in succession into blister pockets. Following the dosing of the two or more layers into the blister pockets the product within the blister pockets is frozen and freeze dried. Each formulation has a sufficiently different density than the other formulation(s) such that they are maintained as separate layers following dosing.

The density of a formulation is modifiable using a suitable soluble density modifier, such as, but not limited to: different buffer salts; different organic weak acids and organic weak bases; and different concentrations for the selected buffer salt and/or weak acid and/or weak base. The use of formulations having two, or more, different densities creates a multi-layer dosage form even when non-gelling matrix formers are used in both formulations.

BRIEF DESCRIPTION OF THE DRAWINGS

FIG. 1 shows the details and results of Example 1.
FIG. 2 shows the details and results of Example 2.
FIGS. 3 and 4 show the details and results of Example 3.

DETAILED DESCRIPTION OF THE INVENTION

Figure 5B:
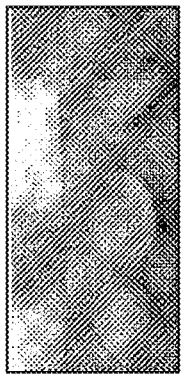
FIG. 5 shows the details and results of Example 4.

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in, other systems and methods. Before explaining the disclosed embodiments of the present invention in detail, it is to be understood that the invention is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an") "'one or more'" and "at least one" can be used interchangeably herein. The terms "comprising", "including", "having" and "constructed from" can also be used interchangeably.

It is to be understood that each component, compound, substituent, or parameter disclosed herein is to be interpreted as being disclosed for use alone or in combination with one or more of each and every other component, compound, substituent, or parameter disclosed herein.

A first embodiment is directed to a method of forming a multi-layer dosage form used for the delivery of an active ingredient such as an active pharmaceutical ingredient ("API"). This embodiment comprises the sequential steps of providing a first formulation to a preformed mold, providing a second formulation to the same preformed mold, freezing the first and second formulations and then freeze-drying to form a multi-layer dosage form.

As used herein, "dosed" refers to the deposition of an aliquot of solution or suspension.

As used herein, "preformed mold" refers to any suitable container or compartment into which an aqueous solution or suspension may be deposited and subsequently frozen and freeze dried. Preferably, in certain disclosed embodiments the preformed mold is a blister pack with one or more blister pockets on aluminum trays.

"Sequentially dosed" or "dosed sequentially" as used herein refers to a process of dosing a first formulation followed by dosing a second, different formulation. Although the dosing is described as "sequential" throughout the description the dosing of the first and second formulations may also be provided simultaneously to a preformed mold. Additionally, the formulations can be added to the mold in any order. Specifically, if a formulation is described as a "first" formulation it may be added before, after, or at the same time as a formulation described as a "second" formulation.

In the first step of one embodiment, a first formulation comprising a non-gelling matrix forming agent is dosed into a preformed mold, followed by dosing a second formulation comprising a non-gelling matrix forming agent into the preformed mold. The first and second formulations have different densities such that a two layer dosage form is obtained.

As used herein, "non-gelling matrix forming agent" refers to a polymer having a ratio of viscosity at 5° C. to viscosity at 25° C. of 4 or less. Viscosity may be determined by a Haake™ VT550 viscotester fitted with an NV rotational sensor or other conventional viscometer. Whether a polymer is a gelling or a non-gelling matrix forming agent depends not only on the chemical nature of the polymer, but also on concentration and other formulation components. Molecular modifications (e.g. depolymerization through hydrolysis, or derivation of the side chain groups), concentration, as well as the absence of other molecules that may induce gelation (e.g., potassium ion for carrageenan, calcium for alginate), may be used to transform gelling polymers into non-gelling polymers in a particular environment by ensuring that gelation does not occur in that environment.

Any conventional non-gelling matrix forming agent may be used for the purposes of the present invention. Suitable non-gelling matrix forming agents include, without limitation, non-gelling gelatins, modified starches, pullulan, non-gelling fish gelatin), maltodextrins, low molecular weight dextrans, starch ethers, low to intermediate molecular weight cellulose gum, and combinations thereof. The amount of non-gelling matrix forming agent present in each of the formulations ranges from about 1% to about 20%, more preferably from about 2% to about 15%, and most preferably from about 4% to about 10% based on the weight of the formulation prior to the removal of water during freeze drying.

Each formulation is typically prepared in the form of a solution or suspension. Accordingly, a solvent is also present in each formulation. A suitable solvent may be readily chosen by one of ordinary skill in the art once the final composition of the formulation is known, and the solvent choice can be based on a variety of factors such as the chosen API, excipient, etc. that is present in the formulation. Preferred solvents include ethanol, isopropanol, other lower alkanols and water, and more preferably, water. The amount of solvent present in each formulation may range from about 50% to about 98%, more preferably from about 65% to about 98%, and most preferably from about 75% to about 95% based on the total weight of the formulation.

One or more of the formulations in the present embodiment can comprise a density modifier. A "density modifier" refers to a compound that can be added to a composition to alter its density, preferably increasing the density of the composition. Any suitable density modifier can be used in one or more of the formulations as long as it is a pharmaceutically acceptable component. Density modifiers that may preferably be used include buffering salts, organic weak acids and weak bases, other organic and inorganic salts, known density modifying compositions: and combinations thereof. When used in both formulations, the same or different density modifiers can be used and when the same density modifiers are used, they can be used in different concentrations.

The pH range desired for the formulations can be achieved by use of weak acids, buffer salts and weak bases. The pH is adjusted to a pH that is favorable for the stability of the API. Typical pH's are in the range of 3-10, or 4-9, or 5-8, or 6.25 to 7.75. The pH may also be adjusted to adjust the absorption of an API once ingested.

A typical formulation without a density modifier will have an average density of about 1.025 g/ml. The density range of the solution after addition of the density modifier will depend on the type of modifier and the concentration. Generally, sufficient density modifier in an amount from about 0.5% to about 20% by weight or from about 1% to about 15% by weight, based on the total weight of the formulation prior to removal of water by freeze drying will be added to increase the density of the solution. Based on this, the increased density formulations will have a density greater than 1.025 g/ml or at least 1.03 g/ml or at least 1.05 g/ml, up to about 1.5 g/ml or more. The density difference sufficient to form two layers can be from 0.005 g/ml to 0.475 g/ml. More preferably, the density difference may be in the range of 0.005 g/ml to 0.075 g/ml since this provides a sufficient different to form two layers while minimizing the amount of the density modifier that needs to be added to the formulation.

When present, the density modifier is present in an amount ranging preferably from about 0.5% to about 20%, more preferably from about 0.5% to about 15%, and most preferably, from about 0.5% to about 10% based on the weight of the formulation prior to the removal of water during freeze drying. The amount of density modifier added to each formulation is such that each formulation has a different density than the other formulations. Preferably, only one formulation contains a density modifier. More preferably, only the first dosed formulation contains a density modifier. Preferably, the density modifier is soluble in the formulation.

The density modifier creates a formulation having a different density than the same formulation without the density modifier. The formulation with the higher density sinks to the bottom of the preformed mold. After the freeze drying process is completed the density difference between the formulations manifests as separate layers within the final dosage form.

Each formulation may also contain one or more pharmaceutically acceptable agent(s) or excipient(s). Such additional pharmaceutically acceptable agents or excipients include, without limitation, sugars, such as mannitol, dextrose, and lactose, inorganic salts, such as sodium chloride and aluminum silicates, gelatins of mammalian origin, fish gelatin, modified starches, preservatives, antioxidants, surfactants, viscosity enhancers, coloring agents, flavoring agents, pH modifiers, sweeteners, taste-masking agents, and combinations thereof. Suitable coloring agents include red, black and yellow iron oxides and FD & C dyes such as FD & C Blue No. 2 and FD & C Red No. 40, and combinations thereof. Suitable flavoring agents include mint, raspberry, licorice, orange, lemon, grapefruit, caramel, vanilla, cherry and grape flavors and combinations thereof.

Suitable pH modifiers include citric acid, tartaric acid, phosphoric acid, hydrochloric acid, maleic acid, sodium hydroxide, and combinations thereof. The pH can be modified to a pH favorable to the stability of the API, to alter absorption characteristics after ingestion such as promoting pre-gastric absorption of selegiline HCl.

In one preferred embodiment of the invention, the active ingredient is a selegiline HCl which is used in the treatment of Parkinson's disease.

Since the system of the present invention contains at least two distinct layers, it is possible to employ selegiline HCl in one layer and a basic buffer in the other layer. For instance, it is often desirable to employ a selegiline salt, such as selegiline HCl in the drug delivery system since such salts are generally more stable than selegiline base. The selegiline salt must first be converted to selegiline base in situ before absorption can occur. In some instances, therefore, it is desirable to incorporate a basic material, such as the basis buffer sodium bicarbonate, in the drug delivery system since the conversion of selegiline salt to selegiline base proceeds more quickly at increased pH. However, due to the relative instability of selegiline base, it is preferred that the conversion of selegiline salt to selegiline base occur in the mouth. As a result, it is preferable to incorporate the selegiline HCl in one layer and the basic buffer in the other layer. Upon contact with saliva, the reaction of the selegiline salt and the layer containing the basic buffer occurs quickly thus increasing the potential for pre-gastric absorption.

Suitable sweeteners include aspartame, acesulfame K, sucralose, thaumatin, and combinations thereof. Suitable taste-masking agents include sodium bicarbonate, ion-exchange resins, cyclodextrin inclusion compounds, adsorbates or microencapsulated actives, and combinations thereof. One of ordinary skill in the art can readily determine suitable amounts of these various additional excipients if desired.

Mannitol is a preferred additional pharmaceutically acceptable agent. When present, an additional pharmaceutically acceptable agent, preferably mannitol, is present in one or both formulations in an amount ranging preferably from about 0% to about 10%, more preferably from about 2% to about 8%, and most preferably from about 3% to about 6% based on the weight of the formulation prior to removal of water during freeze drying.

Each formulation may also contain an active ingredient such as an active pharmaceutical ingredient (API). An API refers to a drug product that may be used in the diagnosis, cure, mitigation, treatment, or prevention of disease. Any API may be used with this invention. One of ordinary skill in the art would understand that for various reasons such as stability, compatibility with other ingredients, desired drug release profile, certain active ingredients and/or APIs are more desirable for formulation into a multi-layer dosage form.

Active ingredients may include pharmaceutical ingredients as well as other types of active ingredients that may be ingested, such as vitamins and dietary supplements.

Suitable APIs include, without limitation: analgesics and anti-inflammatory agents, antacids, anthelmintics, anti-arrhythmic agents, anti-bacterial agents, anti-coagulants, anti-depressants, anti-diabetics, anti-diarrheals, anti-pileptics, anti-fungal agents, anti-gout agents, anti-hypertensive agents, anti-malarials, anti-migraine agents, anti-muscarinic agents, anti-neoplastic agents and immunosuppressants, anti-protazoal agents, anti-rheumatics, anti-thyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, lipid regulating agents, local anesthetics, neuro muscular agents, nitrates and anti-anginal agents, nutritional agents, opioid analgesics, oral vaccines, proteins, peptides and recombinant drugs, sex hormones and contraceptives, spermicides, stimulants, smoking cessation products and combinations thereof. A list of specific examples of active ingredients may be found in U.S. Pat. No. 6,709,669 and U.S. Patent Application Publication No. 2011/0229573, both of which are incorporated herein by reference.

When present, an API is employed in the formulation in an amount that is necessary to provide the dosage required, typically for producing at least one physiological effect as established by clinical studies. One of ordinary skill in the art can readily determine an appropriate amount of active ingredient to include in the multi-layer dosage form made according to the present disclosure. Typically, the API will be present in amounts up to about 400 mg in the final dosage form, and often up to about 200 mg in the final dosage form.

The active pharmaceutical ingredient may be coated with one or more coating layers. Alternatively, the active pharmaceutical ingredient may be complexed with one or more complexing agents. In such embodiments, the complexing agent may comprise cyclodextrin. The complexed active pharmaceutical ingredient may alternatively be complexed with an ion exchange resin. The coatings or complexes can be employed, for example, for modified release and/or for alteration of the taste of the composition.

Each formulation may be formed according to any conventional method. Most typically, the non-gelling matrix forming agent, solvent and optional ingredients may be mixed together at any temperature at which they are stable, though the mixing temperature is preferably between 40° C. and 80° C., to form a solution. The solution may then be cooled to ambient temperature, preferably from about 5° C. to about 30° C., more preferably from about 10° C. to about 30° C., and more preferably from about 15° C. to about 30° C., at which point the active ingredients may be added.

In a preferred embodiment the first formulation is dosed into a preformed mold in a first step. In a second step, a second formulation having a different density than the first formulation is dosed into the same preformed mold. Both dosing steps may be performed at the same, or at different temperatures. Preferably, both dosing steps occur at a temperature close to ambient temperature of from about 5° C. to about 30° C., preferably from about 10° C. to about 30° C. and more preferably from about 15° C. to about 30° C.

In a preferred embodiment, the first formulation comprises a non-gelling matrix forming agent, mannitol, a density modifier, water, and in some embodiments an additional pharmaceutically acceptable excipient. Preferably, this formulation comprises from about 1% to about 20% non-gelling matrix forming agent, about 0% to about 10% mannitol, about 0.5% to about 20% density modifier, about 50% to about 98% water, and about 0% to about 50% of an excipient, more preferably from about 2% to about 15% non-gelling matrix forming agent, about 2% to about 8% mannitol, about 0.5% to about 15% density modifier, about 65% to about 98% water, and about 0% to about 20% of an excipient, and most preferably from about 4% to about 10% non-gelling matrix forming agent, about 3% to about 6% mannitol, about 0.5% to about 10% density modifier, about 75% to about 95% water, and about 0% to about 10% of an excipient. In some embodiments, the first formulation comprises about 80-95%, about 80-90%, or about 85-90% solvent. In some embodiments, the first formulation comprises about 2-10%, about 3-8%, about 5-7%, or about 6% non-gelling matrix forming agent. In some embodiments, the first formulation comprises about 1-5%, about 2-4%, or about 3% pharmaceutically acceptable agent. In some embodiments, the first formulation comprises about 1-5%, about 2-4%, or about 3% density modifier.

In a preferred embodiment, the second formulation comprises a non-gelling matrix forming agent, mannitol, water, and in some embodiments an additional pharmaceutically acceptable excipient. Preferably, this formulation comprises from about 1% to about 20% non-gelling matrix forming agent, about 0% to about 10% mannitol, about 50% to about 98% water, and about 0% to about 50% of an excipient, more preferably from about 2% to about 15% non-gelling matrix forming agent, about 2% to about 8% mannitol, about 65% to about 98% water, and about 0% to about 20% of an excipient, and most preferably from about 4% to about 10% non-gelling matrix forming agent, about 3% to about 6% mannitol, about 75% to about 95% water, and about 0% to about 10% of an excipient. In some embodiments, the second formulation comprises about 80-95%, about 85-95%, about 86-92%, or about 88% solvent. In some embodiments, the second formulation comprises about 2-10%, about 3-8%, about 5-7%, or about 6% non-gelling matrix forming agent. In some embodiments, the second formulation comprises about 1-5%, about 2-4%, or about 3% pharmaceutically acceptable agent.

In a first step the first formulation may be dosed into a preformed mold in an amount of about 10 mg to about 20 mg, about 20 mg to about 1000 mg, more preferably in an amount from about 50 mg to about 500 mg, and most preferably in an amount from about 150 mg to about 300 mg wet dosing.

In a second step the second formulation is dosed into the same preformed mold in an amount of about 10 mg to about 20 mg, about 20 mg to about 1000 mg, more preferably in an amount from about 50 mg to about 500 mg, and most preferably in an amount from about 150 mg to about 300 mg wet dosing.

In a third step, the combination of the formulations dosed in the first and second steps are frozen. The freezing step is preferably carried out rapidly by, for example, freezing in a period of 1-10 minutes using very low temperatures of, for example <−70° C. Typically, the dosed formulations are frozen in the preformed molds by any suitable means known in the art, such as by passing them through a liquid nitrogen tunnel, preferably for about 1 to about 10 minutes or by inserting them into a nitrogen spray freezing chamber, or cooling by passing them over a cold surface.

Finally, the frozen formulations are freeze dried to form the multi-layered dosage form. The dosed formulations in the preformed molds are then freeze dried under vacuum using any suitable, conventional freeze drying method. The freeze-drying process such as is used to make the Zydis® dosage form is often preferred and is incorporated by reference herein. In a preferred method, the solvent is sublimed in a freeze drying process under a reduced pressure which transforms the solid solvent directly into a vapor. The freeze drying process will generally be carried out in a freeze drying chamber typically operating under a vacuum of 0.1 to 1.0 mbar for a period of time from 180 to 500 minutes.

As used herein, the term "bottom layer" refers to a layer formed within a preformed mold having a higher density than that of the "top layer." The higher density may be a result of different, or more density modifier being used in the formulation that forms the bottom layer. The bottom layer may be formed from the first or the second formulation, depending on the relative densities of the formulations. Likewise, the top layer may be formed by either the first or the second formulation, also depending on the relative densities of the formulations.

As described above, the top and bottom layers are formed after the first and second dosing steps are performed. Depending on the relative densities of the first and second formulations as compared to one another, the denser formulation will form the bottom layer, with the lower density formulation forming the top layer. In a preferred embodiment, the first formulation, which is preferably dosed first, forms the bottom layer, and the second formulation which is dosed second, forms the top layer.

As used herein, the term "non-gelled matrix layer" refers to a layer formed within a preformed mold, said layer comprising a non-gelling matrix forming agent, and, optionally, solvents, APIs, excipients and/or other matrix forming agents. The non-gelled matrix layer may be made by sequential dosing into a preformed mold, freezing and freeze drying as described above. In a preferred embodiment, two or more layers that are considered non-gelled matrix layers are sequentially dosed into the preformed mold prior to the freezing and freeze drying steps.

The details noted above regarding the identification of APIs, non-gelling matrix forming agents, preformed molds, additional pharmaceutically acceptable agents, excipients, ingredients, etc. are the same for other embodiments of the disclosure.

The invention also relates to a multi-layer dosage form made according to any of the methods described above. In one aspect, the invention relates to a multi-layer, lyophilized, dosage form for the delivery of at least one active pharmaceutical ingredient comprising:

a) a first non-gelled matrix layer including an active pharmaceutical ingredient; and b) a second non-gelled matrix layer.

In some embodiments, the second non-gelled matrix layer comprises a second active pharmaceutical ingredient that is different from the active pharmaceutical ingredient of said first non-gelled matrix layer. The table below provides some non-limiting examples of embodiments wherein the second matrix layer contains a different API that is incompatible with the API in the first matrix layer.

Examples of Formulations with Incompatible APIs

| Drug | Dosage Form | Rationale | Reference |
|---|---|---|---|
| Montelukast, Levocetrizine | Bilayer tablets | To improve the stability of drugs in combination | Rathod R T, Misra D; FDC of montelukast with levocetrizine: Focus on bilayer technology. |
| Glipizide, Metformin HCI | Bilayer tablets | To avoid interaction between incompatible drugs | Kadam V V, Waghmare M U, Venkatpurwar V P, Pokharkar V B; Preparation and evaluation of glipizide-metformin HCI sustained release bilayer table. Available from www.scientificipca.org/ |
| Telmisartan Hydrochlorthiazide | Bilayer tablets | To minimize contact between hydrochlorothiazide and basic component of telmisartan | Friedl T. Schepky G inventors; Boehringer Ingelheim USA Corporation, assignee: Bilayer pharmaceutical tablet comprising telmisartan and a diuretic and preparation thereof. US 2009/0227802 A1. |
| Amlodipine, Atenolol | Bilayer tablets | To improve the stability of drugs in combination | Aryal S, Skalko-Basnet N; Stability of amlodipine besylate and atenolol in multicomponent tablets of mono-layer and bilayer types. Acta Pharm., 2008; 58: 299-308. |
| Misorostol Diclofenac | Bilayer tablets | To minimize contact between drugs | Ouali A, Azad A K, inventors; Pharmascience Inc, assignee. Stabilized pharmaceutical composition of nonsteroidal anti-inflammatory agent and a prostaglandin. U.S. Pat. No. 6,287,600 B1. |
| Telmisartan, Simvastatin | Bilayer tablets | To minimize contact b/w Simvastatin & telmisartan | Kohlrausch A, inventor; Boehringer Ingelheim International GmbH, assignee. Bilayer tablet oftelmisartan and simvastatin. US 2006/0078615 A1 |
| Statin Aspirin | Bilayer tablets | To minimize interaction b/w two drugs and side effects due to aspirin | Ullah I and Jain N B, inventors; Bristol-Mayer SquibbCompany, assignee. Pharmaceutical composition containing a combination of a statin and aspirin and method, U.S. Patent No. 6,235,311 B1. |

In other embodiments, the second matrix layer comprises one or more components that are not compatible with the API contained in the first matrix layer.

In certain other embodiments, components are included in the second layer that may influence the dosage release profile of the API. The table below provides some non-limiting examples of embodiments wherein the second matrix layer contains one or more components that influence the dosage release profile of the API.

Examples of Formulations with Components that Influence the Dosage Release Profile

| Drug | Dosage form | Rationale | Reference |
|---|---|---|---|
| Aspirin Isosorbide 5-mono-nitrate | Sustained Bilayer tablets | Treatment of pain, fever and other inflammatory conditions | Hu L, Hu Q, Kong D; Formulation and in vitro evaluation of Aspirin and Isosorbide 5-mononitrate sustained bilayer tablets. IJPSR, 2014; 5(3): 799-804. |
| Losartan | Bilayer tablets | Biphasic release profile | Hiremath, D, Gaudanavar P, Azharuddin M, Udupi R H, Sarfaraz M; Design and characterization of bilayer controlled release matrix tablets of losartan potassium. Int J Pharm Res., 2010; 2(4): 34-39. |
| Pioglitazone HCI and Metformin HCI | Bilayer tablet | Synergistic effects or biphasic drug | Kotta, M., Reddy, N., Naga, R. K. Formulation and Evaluation of Bilayer Matrix Tablet of Pioglitazone Hcl Metformin Hcl Usp 15 mg&500 mg Asian J Pharm Clin Res 2013; 6(3): 155-161. |

In the multi-layer, lyophilized dosage forms described in the additional embodiments below, the ratio of the weight of the first layer to the weight of the second layer preferably ranges from about 1:5 to about 5:1, more preferably from about 1:4 to about 4:1, more preferably 1:3 to 3:1, even more preferably from about 1:2 to about 2:1 or about 1:1.

The dosage forms described herein may be used to provide APIs through oral, sublingual, buccal or other known routes of administration of lyophilized dosage forms. The dosage forms comprise a network of active ingredients and a hydrophobic or hydrophilic carrier, which is inert toward the active ingredient. The network is obtained by subliming solvent from a composition in the solid state, that composition comprising the active ingredient and a solution of the carrier in a solvent. The dosage form is similar to that described in U.S. Patent Application Publication No. 2011/0229573, and also U.K. Patent No. 1,548,022, which are both incorporated herein by reference with respect to the description of the dosage form.

The multi-layer dosage form described herein is flexible delivery system due to its multi-layer composition. It is possible to use two or more incompatible APIs or excipients in the dosage form, since each may be placed in its own independent layer, and diffusion across the interface between layers is minimized. Furthermore, it is possible to use a non-gelling matrix forming agent in each layer. Therefore, APIs and excipients that are not compatible with gelling matrix forming agents can be included in this dosage form. The advantage of having all layers utilizing non-gelling matrix forming agents (i.e. effective with biological products due to ability to process the mixture at low temperature such as 10-20'C) in a lyophilized dosage form may be achieved by the present invention.

Examples of excipients that may be employed in the compositions of the present invention may include gums, acacia, agar, alginate, carrageenan, dextran, cellulosic excipients such as methylcellulose, hydroxyl methylcellulose, hydroxyethyl cellulose, and hydroxylpropyl methylcellulose, Carbomers, povidone, co-povidone, polycarbophil, and polyvinylacetate.

Although the invention has been described in the context of a first and a second formulation, the invention is not limited to only the use of two formulations. In general, certain embodiments of the invention may be used to form multi-layer dosage forms, and the use of three or more different formulations may be used to achieve the multi-layer dosage form. To produce a multi-layer dosage form each formulation has a different density, which can be achieved by using varying amounts of, or different density modifiers in each formulation.

The following examples are illustrative, but not limiting, of the tablets of the present disclosure. Other suitable modifications and adaptations of the variety of conditions and parameters normally encountered in the field, and which are obvious to those skilled in the art, are within the scope of the disclosure.

EXAMPLES

The present invention is not limited to any specific API, but instead provides a solution to problems exhibited by certain types APIs by providing methods suitable for formulating such APIs in a multi-layer dosage form. The following examples illustrate the practice of the present invention in some of the preferred embodiments.

For the following examples, viscosity was determined using a Haake™ VT550 Viscotester fitted with a NV rotational sensor. The viscosity was recorded at shear rates between 500 and 2500 (1/s) with the temperature of the sensor maintained at the same temperature as the temperature of the sample.

For the following examples, density was measured in air at 20° C. using a pycnometer to determine the weight of the liquid per unit volume in g/ml. The following method was used to determine the density of each of the formulations.
1. Weigh an empty, clean, dry pycnometer with the glass stopper in place.
2. Fill the pycnometer with the formulation being tested and replace the stopper. Remove any excess liquid from the outside of the pycnometer and weigh.
3. Remove the test formulation from the pycnometer. Clean and dry thoroughly.
4. Repeat the above operations 1-3 using water in place of the formulation being tested.
5. Calculate the capacity of the pycnometer according to the following:

Capacity ($P_c$) (ml at 20° C.)=(measured weight water in g*1000)/997.18 g.

997.18 g is the weight of 1 liter of water at 20° C.
6. Calculate the weight per milliliter of the formulation being tested using the following equation:

Weight/milliliter (density)=$(P_L-P)/P_c$ (g/ml) Where:

P=The weight of the empty pycnometer, in g.
$P_L$=The weight of the pycnometer filled with the formulation under test in g.
$P_c$=The capacity of the pycnometer, in ml.

Experimental Procedure

A lyophilized two-layer tablet of a kind known in the art was prepared. The prior art two-layer tablet was formed by sequentially dosing two formulations into preformed blister pockets on aluminum trays. Once both layers were dosed, the material was rapidly frozen at <−70° C. using liquid nitrogen for 3 minutes. Then, the composition was freeze dried. The dosage form employed non-gelling matrix former(s) in both layers. Placebo formulations and formulations having model APIs are also exemplified. The model APIs evaluated as examples herein include: diphenhydramine HCl; Selegiline HCl; and Thiamine HCl.

Fish gelatin was used as matrix former in combination with mannitol.

An aliquot of either 200 mg or 300 mg of each of first and second formulations was dosed to form each layer. In each example, a brilliant blue dye solution was added to the one of the layer formulations to aid visualization of the two layers.

After all formulations were dosed, the material was rapidly frozen at low temperature (<−70° C. using liquid nitrogen for 3 minutes). The frozen products were freeze dried at 0° C. for 12 hours.

Example 1

Using placebo formulations, a comparison was made between use of a viscosity adjustment and a density adjustment to form a two layer tablet. Products 1 and 2 as shown in Table 1 were made using a viscosity adjustment to make the two layer dosage form. Products 3 and 4 in Table 1 were made using a density adjustment to create the two layer dosage form. The Experimental Procedure described above was used with the modifications indicated below.

To adjust the viscosity of Products 1 and 2, the dosing temperature of the formulations was adjusted. For the first dosing layer, dosing temperatures of 14° C. and 8° C. were used for Products 1 and 2, respectively. For the second dosing layer, a dosing temperature of 23° C. was used for both Products 1 and 2. Lowering the dosing temperature increases the viscosity of the formulation during dosing as shown in Table 1. The viscosity and the pH of each layer were measured. Following freeze drying, Products 1 and 2 were inspected for appearance (see Table 2 of FIG. 1).

For Products 3 and 4, a different density was achieved in each formulation by addition of a buffer salt to one of the two layers. For Products 3 and 4, 5% w/w and 1% w/w of the buffer salt were added to the first formulation, respectively. No buffer salt was added to the second formulation. The difference in density for the two layers is shown in Table 1. The viscosity, pH and density of each layer were measured. Following freeze drying, Products 3 and 4 were inspected for appearance (see Table 2 of FIG. 1).

The results obtained with Products 3 and 4 show that a small differential difference in the formulation density as shown in Table 1 is sufficient to maintain the separation of the two formulations during manufacture of the tablet to thereby provide a freeze dried two layer tablet using a standard freeze-drying dosage form manufacturing process.

TABLE 1

|  | Product 1 | | Product 2 | | Product 3 | | Product 4 | |
| --- | --- | --- | --- | --- | --- | --- | --- | --- |
| | Layer Number [Formulation Nos] | | | | | | | |
| | 1st dosing layer [JZ1/28/2] | 2nd dosing layer [JZ1/28/3] | 1st dosing Layer [JZ1/28/2] | 2nd dosing layer [JZ1/28/3] | 1st dosing Layer [JZ1/28/2] | 2nd dosing layer [JZ1/28/3] | 1st dosing Layer [JZ1/28/2] | 2nd dosing layer [JZ1/28/3] |
| | Dosing temp (° C.) | | | | | | | |
| | 14 | 23 | 8 | 23 | 23 | 23 | 23 | 23 |
| | Aliquot Dosing weight (mg) | | | | | | | |
| | 300 | 300 | 300 | 300 | 300 | 300 | 300 | 300 |
| Composition | | | | | | | | |
| Fish gelatin | 5% | 5% | 5% | 5% | 5% | 5% | 5% | 5% |
| Mannitol | 3% | 3% | 3% | 3% | 3% | 3% | 3% | 3% |
| Sodium phosphate | 0% | 0% | 0% | 0% | 5% | 0% | 1.0% | 0% |
| Brilliant Blue | 0.01% | N/A | 0.01% | N/A | 0.01% | N/A | 0.01% | N/A |
| Testing | | | | | | | | |
| pH | N/R | 6.45 | N/R | 6.45 | 8.50 | 6.45 | 8.17 | 6.47 |
| Overall pH upon reconstitution of tablet | N/R | | N/R | | 8.32 | | 7.82 | |
| Viscosity (mPa · s) | 12.1 | 7.4 | 30.7 | 7.4 | 9.1 | 7.6 | 8.2 | 7.6 |
| Viscosity difference between layers | 4.7 mPa · s | | 23.3 mPa · s | | 1.5 mPa · s | | 0.6 mPa · s | |
| Solution Density (g/ml) | 1.024 | 1.024 | 1.026 | 1.024 | 1.074 | 1.024 | 1.033 | 1.024 |
| Density difference between layer (g/ml) | 0.000 | | 0.002 | | 0.024 | | 0.009 | |

Example 1 shows that a formulation containing 5% fish gelatin and 3% mannitol (Products 1 and 2, respectively), when dosed at different viscosities achieved by adjusting the dosing temperatures, the desired freeze dried tablet having two distinct layers was not successfully formed. For instance in Product 2, sequentially dosing a first layer at 8° C. and a second layer at 23° C. to achieve a viscosity differential of 23 mPa·s did not provide a tablet having two distinct layers. These results demonstrate that it is not always feasible to achieve a bilayer freeze dried tablet using sequential dosing of two formulations having different viscosities using different dosing temperatures.

Example 1 also shows that a freeze dried tablet with two distinct layers can be achieved by sequential dosing of two formulations followed by freezing and freeze drying, by including a buffer salt, such as sodium phosphate dibasic in one of the formulations to provide a density difference between the first and second formulations. The addition of the buffer salt resulted in a very minor viscosity increase of <3 mPa·s in the formulation. It was expected that this small difference in viscosity would not be sufficient to form two distinct layers, based on the results obtained for comparative Products 1 and 2 since the viscosity difference employed for Products 1 and 2 was significantly larger. Surprisingly, Products 3 and 4 formed two distinct layers despite the relatively smaller difference in viscosity between the first and second formulations.

Example 2

Example 2 evaluated the effect of the sequence of dosing formulations having different densities on the formation of a bilayer or two layer tablet. Two layer dosage forms were manufactured using the Experimental Procedure described above. The formulations contained 5% fish gelatin and 3% mannitol. The product was sequentially dosed with either: (a) first layer dosing with a formulation containing buffer salt followed by second layer dosing of the same formulation without buffer salt (Products 5 and 7), or (b) first layer dosing with a formulation without buffer salt and second layer dosing with a formulation containing buffer salt (Products 6 and 8). Brilliant blue dye solution was added to the formulation without the buffer salt.

The pH and viscosity of the formulations for each layer are summarized in Table 3 of FIG. 2. Following freeze drying, the dosage forms were inspected for appearance.

Example 2 confirmed the results of Example 1, and further demonstrated that the addition of buffer salt to the base formulation increased the density and that the density difference is sufficient to maintain the separation of two sequentially dosed formulations dosed in either order. When dosed formulations are frozen and freeze dried, a two layer dried tablet is formed. Also shown by the results of Example 2 was that the denser of the two formulations was formed as the bottom layer of the tablet irrespective of the order of the dosing sequence. As seen in Table 3 of FIG. 2, the formulation having the blue dye was the bottom layer in all Products.

Example 3

The two layer tablets of Example 3 were manufactured using the Experimental Procedure described above. However, in Example 3, the formulations contained 6% w/w fish gelatin and 3% w/w mannitol.

The product was sequentially dosed. The formulation for the first layer dosing contained buffer salt at three different concentrations (3%, 5%, and 7%, Products 9, 10, and 11, respectively). Brilliant blue dye solution was added to the formulation without buffer salt to aid in visualization of the layer and this was dosed as the second layer. The viscosity of the formulation for each layer was measured. For each layer, 300 mg of the formulation was dosed. The dosed product was rapidly frozen at low temperature (<−70° C. using liquid nitrogen for 3 minutes). The frozen products were freeze dried at 0° C. for 12 hours. Following freeze drying, the tablets were inspected for appearance. The results are shown in Table 4 of FIG. 3.

The sequence of dosing was also reversed using the same formulations. The results are shown as Products 12-14 on Table 5 of FIG. 4. Despite the reverse dosing sequence, the denser formulation containing the buffer salt still formed the bottom layer of the two layer tablet.

Example 4

A two layer tablet was manufactured according to the Experimental Procedure described above and as in Example 1. In this example a model drug was used in place of the placebo used in the previous examples. Diphenhydramine HCl was used as the model soluble drug for this example. Use of the drug supplied at 3.3% and 0.04% in solution was evaluated, using fish gelatin as the non-gelling matrix forming agent. The results are shown in Table 6 of FIG. 5. The density modifier was added to the first formulation, and the soluble model drug was added to the second formulation.

The results show that a bilayer tablet having distinct layers was formed when a model soluble drug was contained in the second formulation. The denser formulation, containing the buffer salt, was formed as the bottom layer of the two layer tablet.

Example 5

Figure 6B:
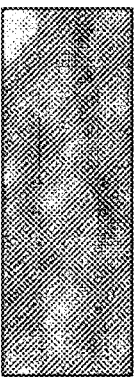
FIGS. 6-7 show the details and results of Example 5.
Figure 7B:
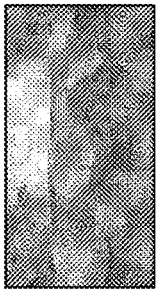

Two layer tablets were manufactured according to the process used in Example 4, but containing a different model drug. In this example, selegiline HCl was used as a model soluble drug. Selegiline HCl was provided at 0.5% and 0.04% in solution, using fish gelatin as the non-gelling matrix forming agent (shown in Tables 7 and 8 of FIGS. 6-7, respectively).

The tables in the Figures show that use of fish gelatin as a non-gelling matrix forming agent with selegiline HCl following the same manufacturing process as previously described produced a two layer tablet having distinct layers. The layer containing the buffer salt was denser and was located as the bottom layer in each tablet.

Example 6

Figure 8B:
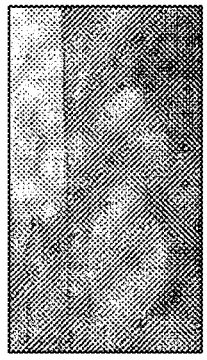
FIG. 8 shows the details and results of Example 6.

Two layer tablets were manufactured according to the Experimental Procedure described above and for Example 2. However, citric acid was used as the density modifier instead of buffer salt. Citric acid was added at concentrations of 5%, 3% and 1% to the formulation containing fish gelatin as the non-gelling matrix forming agent (Products 22, 23 and 24, respectively). The results are shown in Table 9 of FIG. 8. Product 24 also contained 0.4% in solution of Thiamine HCl as a model soluble drug. Brilliant blue dye was added to the layer that did not contain the citric acid to aid in visualization.

The formed two layer tablets showed two distinct layers with the denser layer containing the citric acid located as the bottom layer.

Example 7

Figure 9:
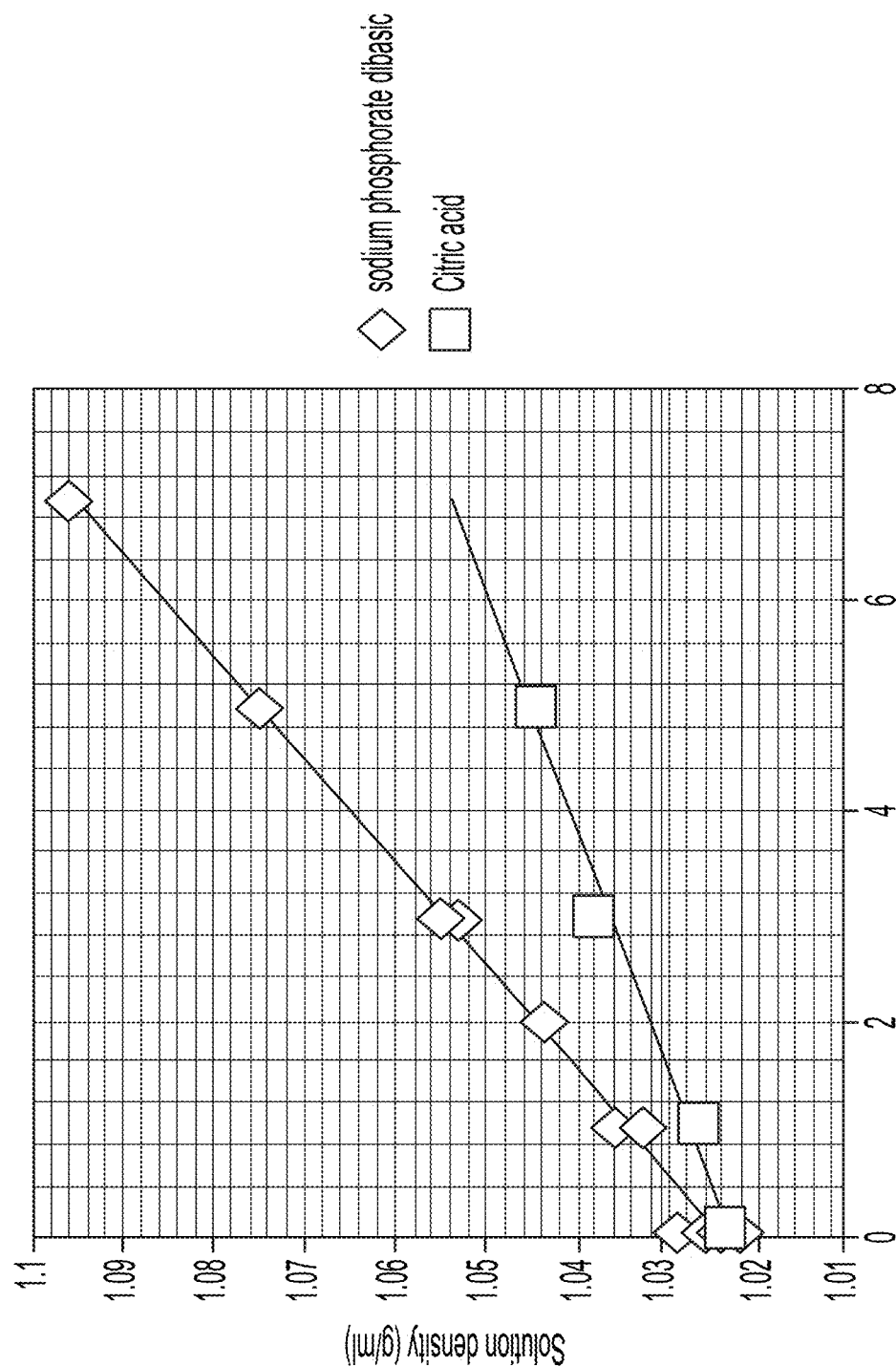
FIG. 9 shows a graph of the density increase as a function of the concentrations of two different density modifiers used in the formulations.

Two formulations were prepared each with densities of about 1.025 g/ml. To one formulation was added several different concentrations of sodium phosphorate dibasic as a density modifier. To the other formulation was added several different concentrations of citric acid as a density modifier. The densities of the formulations containing different concentrations of the two density modifiers are shown in FIG. 9. From FIG. 9 it can be seen that density increase is a linear function of the concentration of the density modifier in the formulation.

Examples 8-10

The following three examples were prepared using the same methodology as explained above. The completed mixes were stirred for approximately 24 hours prior to dosing.

Example 8 is a bilayer tablet containing vitamin B12 in lower density layer and vitamin C in higher density layer (density modified with citric acid).

Vitamin C Layer

| Material name | % by weight | mg/tablet |
| --- | --- | --- |
| Purified water EP/USP | 85.00 | 425.00* |
| Gelatin USP/EP/JP (Fish Std HMW) | 6.00 | 30.00 |
| Mannitol EP/USP/JP | 3.00 | 15.00 |
| Citric acid | 3.00 | 15.00 |
| Vitamin C | 3.00 | 15.00 |
| Total | 100.00 | 500.00 |

*removed during freeze drying

Vitamin B12 Layer

| Material name | % by weight | mg/tablet |
| --- | --- | --- |
| Purified water EP/USP | 88.00 | 440.00* |
| Gelatin USP/EP/JP (Fish Std HMW) | 6.00 | 30.00 |
| Mannitol EP/USP/JP | 3.00 | 15.00 |
| Vitamin B12 (1% powder) | 3.00 | 15.00** |
| Total | 100.00 | 500.00 |

*removed during freeze drying
**Equal to 150 μg of vitamin B12

Both batches were stirred separately for ~24 hours prior to dosing into the same blister pocket prior to freezing and freeze drying. The density differences meant that there was minimal mixing of the two layers prior to Freezing.

Example 9 is a bilayer tablet containing vitamin B12 in high density layer (density modified with sodium phosphate dibasic) and vitamin C in lower density layer.

Vitamin B12 Layer

| Material name | % by weight | mg/tablet |
|---|---|---|
| Purified water EP/USP | 85.00 | 425.00* |
| Gelatin USP/EP/JP (Fish Std HMW) | 6.00 | 30.00 |
| Mannitol EP/USP/JP | 3.00 | 15.00 |
| Sodium phosphate dibasic(as hydrate 12H20) | 3.00 | 15.00 |
| Vitamin B12 (1% powder) | 3.00 | 15.00** |
| Total | 100.00 | 500.00 |

*removed during freeze drying

Vitamin C Layer

| Material name | % by weight | mg/tablet |
|---|---|---|
| Purified water EP/USP | 88.00 | 440.00* |
| Gelatin USP/EP/JP (Fish Std HMW) | 6.00 | 30.00 |
| Mannitol EP/USP/JP | 3.00 | 15.00 |
| Vitamin C | 3.00 | 15.00 |
| Total | 100.00 | 500.00 |

*removed during freeze drying
** Equal to 150 µg of vitamin B12

Both batches were stirred separately for ~24 hours prior to dosing into the same blister pocket prior to freezing and freeze drying. The density differences meant that there was minimal mixing of the two layers prior to Freezing.

Example 10 is a control batch employing a single tablet containing vitamin B12 and vitamin C with no density modifiers.

| Material name | % by weight | mg/tablet |
|---|---|---|
| Purified water EP/USP | 88.00 | 880.00* |
| Gelatin USP/EP/JP (Fish Std HMW) | 6.00 | 60.00 |
| Mannitol EP/USP/JP | 3.00 | 30.00 |
| Vitamin C | 1.50 | 15.00 |
| Vitamin B12 (1% powder) | 1.50 | 15.00** |
| Total | 100.00 | 1000.00 |

*removed during freeze drying
**Equal to 150 µg of vitamin B12

The mix was stirred for ~24 hours prior to dosing therefore allowing the vitamin C and B12 to interact with each other.

The finished product for each of these examples was stored at room temperature (~20° C.) for 22 months prior to analytical testing.

Analytical Testing: The Vitamin B12 potency assay is performed using *Escherichia coli* (ATCC® 14169™ or NCIMB 9270). This strain is modified to grow in the presence of Vitamin B12. The sample is diluted in water to obtain a starting solution of ~0.01 µG and then further down to 0.0025 µg (the lowest sensitivity of the assay). Samples are plated out using Latin Square design and incubated at 31° C. for 18-24 hours. Zones of growth are measured and the potency of the sample is then calculated.

The vitamin C assay method was run using the method below:

7. HPLC Instrument Parameters

| | |
|---|---|
| Column | Gemini 5µ C18 110A for chromatography 4.6 mm × 250 mm (or equivalent) |
| Mobile Phase | 750 ml (0.1M $KH_2PO_4$ aq) + 250 ml (1% w/v m-$H_3PO_4$) |
| Flow Rate | 1.0 ml per minute |
| UV detector | 245 nm |
| Injection | 10 µl loop |
| Run time | 10 mins |
| Column set @ | 35° C. |
| Autosample set @ | 15° C. |

Analytical Results for Examples 8-10

| Example | Vitamin B12 assay (% label claim) | Vitamin C (Assay) (% label claim) |
|---|---|---|
| 8 | 95.1 | 88.1 |
| 9 | 88.3 | 57.5 |
| 10 | 89.3 | 30.1 |

The assay results for both the vitamin B12 and vitamin C demonstrate improved stability for the bilayer formulations versus the single layer formulations. In addition, the improved stability is more substantial for the vitamin C.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

All documents cited herein are hereby incorporated by reference in their entirety.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The above description is presented to enable a person skilled in the art to make and use the disclosure, and is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein. Finally, the entire disclosure of the patents and publications referred in this application are hereby incorporated herein by reference.

What is claimed is:

1. A method of forming a multi-layer dosage form comprising:
   (a) dosing a first formulation comprising 4-10 wt. % non-gelling fish gelatin and 2-8 wt. % mannitol and having a first density into a preformed mold;
   (b) dosing a second formulation comprising 4-10 wt. % non-gelling fish gelatin, 2-8 wt. % mannitol, and 1-7 wt. % of at least one of citric acid or sodium phosphate dibasic and having a second density not equal to the first density into the same preformed mold and a difference between the first density and the second density is 0.005 g/ml to 0.475 g/ml;
   (c) freezing the first and second dosed formulations; and
   (d) freeze drying the frozen first and second formulations to form the multi-layered dosage form.

2. The method according to claim 1, wherein steps a) and b) are carried out at a temperature of from about 5° C. to about 30° C.

3. The method according to claim 1, wherein steps a) and b) are carried out sequentially.

4. The method according to claim 1, wherein one of the first and second formulations contains a first active ingredient.

5. The method according to claim 4, wherein one of the first and second formulations contains a second active ingredient different from the first active ingredient, and wherein the first active ingredient and second active ingredient are in different formulations.

6. The method according to claim 4, wherein one of the first and second formulations contains a material capable of reacting with the active ingredient, and wherein the first active ingredient and the material are in different formulations in its salt form to convert it to a basic form to increase the potential for pre-gastric absorption.

7. The method according to claim 4, wherein the active ingredient is selected from the group consisting of analgesics and anti-inflammatory agents, antacids, anthelmintics, anti arrhythmic agents, anti-bacterial agents, anti-coagulants, anti-depressants, anti-diabetics, antidiarrheals, anti-pileptics, anti-fungal agents, anti-gout agents, anti-hypertensive agents, anti malarials, anti-migraine agents, anti-muscarinic agents, anti-neoplastic agents and immunosuppressants, anti-protazoal agents, anti-rheumatics, anti-thyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti parkinsonian agents, gastro-intestinal agents, histamine receptor antagonists, lipid regulating agents, local anesthetics, neuro muscular agents, nitrates and anti-angina agents, nutritional agents, opioid analgesics, oral vaccines, proteins, peptides and recombinant drugs, sex hormones and contraceptives, spermicides, stimulants, smoking cessation products, vitamins, dietary supplements and combinations thereof.

8. The method according to claim 4, wherein the active ingredient is coated.

9. The method according to claim 4, wherein the active ingredient forms part of a complex.

* * * * *